ic Patent Number: 4,774,338
Date of Patent: Sep. 27, 1988

[54] PREPARATION OF OPTICALLY ACTIVE AZOLE DERIVATIVES

[75] Inventor: Uwe Priesnitz, Solingen, Fed. Rep. of Germany

[73] Assignee: Bayer Aktiengesellschaft, Leverkusen, Fed. Rep. of Germany

[21] Appl. No.: 856,913

[22] Filed: Apr. 28, 1986

[30] Foreign Application Priority Data

May 3, 1985 [DE] Fed. Rep. of Germany ....... 3515869

[51] Int. Cl.⁴ .................. C07D 249/08; C07D 233/60
[52] U.S. Cl. ..................................... 548/262; 548/341; 562/506
[58] Field of Search ................ 562/506; 548/262, 341

[56] References Cited

U.S. PATENT DOCUMENTS 4,024,163 5/1977 Elliott et al. ................ 562/506
4,435,203 3/1984 Yuji Funaki et al. ........... 548/262

FOREIGN PATENT DOCUMENTS 0022972 1/1981 European Pat. Off. ............ 548/262
0102163 3/1984 European Pat. Off. ............ 548/262
0114609 8/1984 European Pat. Off. ............ 548/262
0114608 8/1984 European Pat. Off. ............ 548/262

Primary Examiner—Glennon H. Hollrah
Assistant Examiner—Patricia L. Morris
Attorney, Agent, or Firm—Sprung Horn Kramer & Woods

[57] ABSTRACT

A process for the preparation of a substantially pure optically active azole derivative of the formula

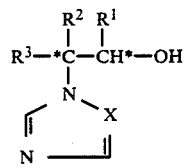

in which $R^1$ and $R^3$ are organic radicals,
$R^2$ is hydrogen or methyl, and
X is N or CH, comprising in a first stage reacting a racemate of an azole derivative of the formula

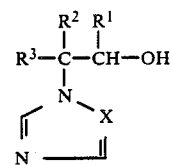

with an optically active permethric acid halide of the formula

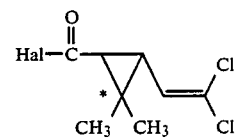

in which
Hal represents chlorine or bromine, thereby to produce a diastereomeric mixture of an ester of the formula

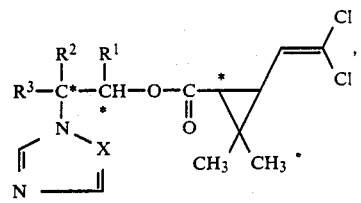

in a second stage separating the components of the ester mixture based on their different physical properties, and in a third stage reacting an individual component ester with a base in the presence of a diluent to liberate the desired substantially pure optically active azole derivative.

6 Claims, 1 Drawing Sheet

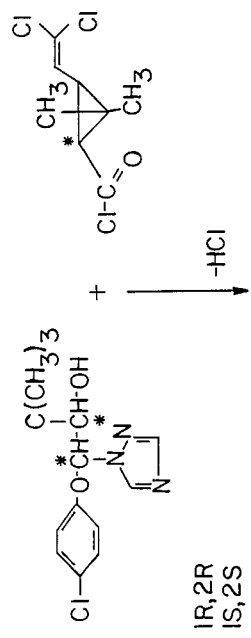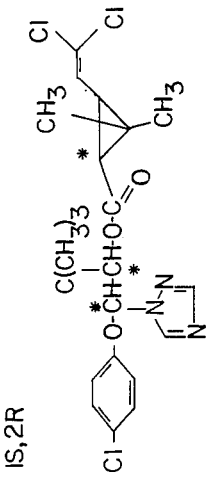

PREPARATION OF OPTICALLY ACTIVE AZOLE DERIVATIVES

The present invention relates to a new process for the preparation of optically active azole derivatives with fungicidal and plant growth-regulating activity.

It is already known that racemates of certain azole derivatives can be resolved into individual enantiomers with the aid of optically active components (compare EP-OS (European Published Specification) No. 0,114,608, EP-OS (European Published Specification) No. 0,114,609 and U.S. Pat. No. 4,435,203). However, these processes have some disadvantages. Thus, the optical purity of the resulting compounds is not always completely satisfactory. In addition, the two enantiomers in question in many cases cannot be prepared equally well, since the two antipodes of the optically active auxiliary reagents required are not always available in a sufficiently pure form. Moreover, the optically active azole derivatives are frequently obtained in a yield which is too low for practical purposes.

It has now been found that optically active azole derivatives of the formula

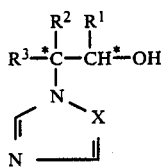
(I)

in which

R$^1$ represents optionally substituted alkyl, optionally substituted cycloalkyl, optionally substituted aryl or optionally substituted heterocyclyl, R$^2$ represent hydrogen or methyl, R$^3$ represents alkyl, alkoxy, cycloalkylalkyl, optionally substituted aryl, optionally substituted aralkyl, optionally substituted aroxy or optionally substituted aroxyalkyl, or R$^2$ and R$^3$ together represent the group of the formula

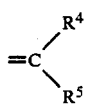

wherein

R$^4$ represents hydrogen, alkyl, cycloalkyl or cycloalkenyl and

R$^5$ represents alkyl, cycloalkyl, cycloalkenyl or optionally substituted aryl, or R$^4$ and R$^5$, together with the carbon atom to which they are bonded, represent cycloalkyl or cycloalkenyl, and X represents nitrogen or a CH group, can be prepared by a process in which, in a first stage, racemates of azole derivatives of the formula

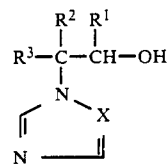
(Ia)

in which

R$^1$, R$^2$, R$^3$ and X have the abovementioned meaning, are reacted with optically active permethric acid halides of the formula

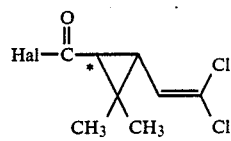
(II)

in which

Hal represents chlorine or bromine, if appropriate in the presence of an acid-binding agent and if appropriate in the presence of a diluent, and then, in a second stage, the diastereomeric esters thus obtained, of the formula

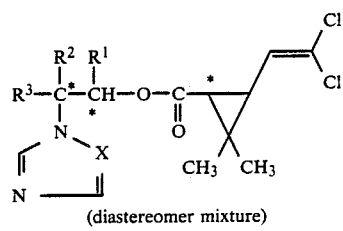
(III)

(diastereomer mixture)

in which

R$^1$, R$^2$, R$^3$ and X have the abovementioned meaning, are separated on the basis of their different physical properties, and, thereafter, in a third stage, the particular azole derivative of the formula (I) is liberated from the corresponding ester with the aid of bases in the presence of a diluent.

In the abovementioned formulae, the asymmetrically substituted carbon atoms are always labelled by an (*) if the compounds are optically active.

It is to be regarded as extremely surprising that numerous optically active azole derivatives can be prepared in a very high yield and excellent optical purity by the process according to the invention, since on the basis of the known prior art, general application of this preparation method was not to be expected.

The process according to the invention has a number of advantages. Thus, the individual enantiomers of the permethric acid halides required as starting substances are also available in an extremely high optical purity on an industrial scale. Diastereomer mixtures of esters of the formula (III) can therefore be prepared in a controlled manner by using one or other of the enantiomers, and from these mixtures the particular ester desired can be removed without difficulties. It is particularly advantageous here that identical separation methods can be used for isolating complementary esters. In general, fractional crystallization is sufficient to separate the desired diastereomeric esters. Moreover, the enantiomers of the permethric acid halides of the formula (II) to be employed can be prepared entirely synthetically. Another advantage of the process according to the invention consists, finally, of the fact that numerous optically active azole derivatives are available in a high yield and excellent optical purity.

The invention will be further described with reference to the accompanying drawing which is a flow sheet of a process in accordance with the invention wherein racemic 1-(4-chlorophenoxy)-1-(1,2,4-triazol-1-yl)-2-hydroxy-3,3-dimethyl-butane and 1R-trans-permethric acid chloride are used as starting substances (1st stage) and a mixture of potassium hydroxide, water and methanol is used for hydrolysis of the ester (3rd stage).

Formula (Ia) provides a definition of the racemates of azole derivatives required as starting substances in carrying out the process according to the invention. Preferably, in this formula, $R^1$ represents straight-chain or branched alkyl with 1 to 4 carbon atoms, or represents cycloalkyl which has 3 to 7 ring carbon atoms and is optionally monosubstituted or polysubstituted by alkyl with 1 or 2 carbon atoms, or represents phenyl or naphthyl, it being possible for the above two radicals mentioned to be monosubstituted or polysubstituted by identical or different substituents from the group comprising halogen, straight-chain or branched alkyl with 1 to 4 carbon atoms and halogenoalkyl with 1 or 2 carbon atoms and 1 to 5 identical or different halogen atoms, such as fluorine and chlorine atoms, or $R^1$ furthermore represents a 5-membered or 6-membered, optionally benzo-fused heterocyclic radical with 1 to 3 identical or different heteroatoms, such as oxygen, nitrogen and sulphur, it being possible for the heterocyclic radical to be monosubstituted or polysubstituted by identical or different substituents from the group comprising halogen, alkyl with 1 to 4 carbon atoms and halogenoalkyl with 1 or 2 carbon atoms and 1 to 5 identical or different halogen atoms, such as fluorine or chlorine atoms, or $R^1$ furthermore represents the radicals of the formulae

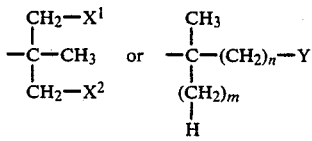

wherein $X^1$ represents hydrogen or halogen, $X^2$ represents halogen,

Y represents straight-chain or branched alkyl with 1 to 6 carbon atoms, alkoxy with 1 to 6 carbon atoms, alkylthio with 1 to 6 carbon atoms, halogenoalkoxy with 1 to 6 carbon atoms and 1 to 9 identical or different halogen atoms, halogenoalkylthio with 1 to 6 carbon atoms and 1 to 9 identical or different halogen atoms, alkenyl with 2 to 6 carbon atoms, straight-chain or branched alkoxycarbonyl with 1 to 4 carbon atoms in the alkoxy part or cyano, or represents phenyl, phenoxy, phenylthio, phenylalkoxy with 1 to 4 carbon atoms in the alkoxy group or phenylalkylthio with 1 to 4 carbon atoms in the alkylthio group, it being possible for each of the abovementioned phenyl radicals to be monosubstituted or polysubstituted by identical or different substituents from the group comprising halogen, alkyl with 1 to 4 carbon atoms, alkoxy with 1 or 2 carbon atoms, alkylthio with 1 or 2 carbon atoms, halogenoalkyl with 1 or 2 carbon atoms and 1 to 5 identical or different halogen atoms, such as fluorine and chlorine atoms, halogenoalkoxy with 1 or 2 carbon atoms and 1 to 5 identical or different halogen atoms, such as fluorine and chlorine atoms, halogenoalkylthio with 1 or 2 carbon atoms and 1 to 5 identical or different halogen atoms, such as fluorine and chlorine atoms, cycloalkyl with 3 to 7 carbon atoms, dialkylamino with 1 to 4 carbon atoms in each alkyl part, cyano, nitro and stright-chain or branched alkoxycarbonyl with 1 to 4 carbon atoms in the alkoxy part, and m represents the number 0 or 1, n represents the number 0, 1 or 2, $R^2$ represents hydrogen or methyl, $R^3$ represents alkyl with 1 to 6 carbon atoms, alkoxy with 1 to 6 carbon atoms, cycloalkylalkyl with 3 to 8 carbon atoms in the cycloalkyl group and 1 to 4 carbon atoms in the alkyl part, aryl which has 6 to 10 carbon atoms and is optionally mono- or polysubstituted by identical or different substituents from the group comprising alkyl with 1 to 4 carbon atoms, halogen, phenyl and/or nitro, or aralkyl which has 6 to 10 carbon atoms in the aryl part and 1 to 4 carbon atoms in the alkyl part and is optionally mono- or polysubstituted by identical or different substituents from the group comprising alkyl with 1 to 4 carbon atoms, halogen, phenyl and/or nitro, or represents aroxy which has 6 to 10 carbon atoms and is optionally mono- or polysubstituted by identical or different substituents from the group comprising alkyl with 1 to 4 carbon atoms, halogen, phenyl and/or nitro, or represents aroxyalkyl which 6 to 10 carbon atoms in the aroxy part and 1 to 4 carbon atoms in the alkyl part and is optionally mono- or polysubstituted by identical or different substituents from the group comprising alkyl with 1 to 4 carbon atoms, halogen, phenyl and/or nitro, or $R^2$ and $R^3$ also together represent the group

in which $R^4$ represents hydrogen, alkyl with 1 to 4 carbon atoms, cycloalkyl with 3 to 8 carbon atoms or cycloalkenyl with 5 to 8 carbon atoms and $R^5$ represents alkyl with 1 to 4 carbon atoms, cycloalkyl with 3 to 8 carbon atoms, cycloalkenyl with 5 to 8 carbon atoms, or aryl which has 6 to 10 carbon atoms and is optionally mono- or polysubstituted by identical by identical or different substituents from the group comprising alkyl with 1 to 4 carbon atoms and/or halogen, or $R^4$ and $R^5$, together with the carbon atoms to which they are bonded, represent cycloalkyl with 5 to 8 carbon atoms, or represents cycloalkenyl with 5 to 8 carbon atoms, and X represents nitrogen or a CH group.

Particularly preferred racemates of azole derivatives of the formula (Ia) are those in which $R^1$ represents methyl, ethyl, n- or i-propyl or n, i-, s- or t-butyl, or represents cyclopropyl, cyclopentyl or cyclohexyl, optionally mono-, di- or trisubstituted by identical or different substituents from the group comprising methyl and/or ethyl, or represents phenyl or naphthyl, it being possible for each of the two abovementioned radicals to be mono-, di- or trisubstituted by identical or different substituents from the group comprising fluorine, chlorine, bromine, iodine, methyl, ethyl, n-propyl, isopropyl, trifluoromethyl and trichloromethyl, or $R^1$ furthermore represents the radicals of the formulae

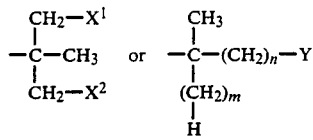

wherein $X^1$ represents hydrogen or halogen, $X^2$ represents halogen,

Y represents methyl, ethyl, n- or i-propyl, methoxy, ethoxy, methylthio, ethylthio, trifluoromethoxy, trifluoromethylthio, vinyl, allyl, methoxycarbonyl, ethoxycarbonyl or cyano, or represents phenyl, phenoxy, phenylthio, benzyloxy or benzylthio, it being possible for each of the five last-mentioned radicals to be mono-, di- or trisubstituted in the phenyl part by identical or different substituents from the group comprising fluorine, chlorine, bromine, methyl, ethyl, methoxy, methylthio, trifluoromethyl, trifluoromethoxy, trifluoromethylthio, dimethylamino, diethylamino, methoxycarbonyl, ethoxycarbonyl, cyano and nitro, m represents the number 0 or 1 and n represents the number 0, 1 or 2, $R^2$ represents hydrogen or methyl, $R^3$ represents alkyl with 1 to 4 carbon atoms, alkoxy with 1 to 4 carbon atoms, cycloalkylalkyl with 5 to 7 carbon atoms in the cycloalkyl part and 1 to 3 carbon atoms in the alkyl part or phenyl which is optionally mono-, di- or trisubstituted by identical or different substituents from the group comprising methyl, ethyl, propyl, fluorine, chlorine, bromine, phenyl and/or nitro, or represents phenylalkyl which has 1 or 2 carbon atoms in the alkyl part and is optionally mono-, di- or trisubstituted by identical or different substituents from the group comprising methyl, ethyl, propyl, fluorine, chlorine, bromine, phenyl and/or nitro, or represents phenoxy which is optionally mono-, di- or trisubstituted by identical or different substituents from the group comprising methyl, ethyl, propyl, fluorine, chlorine, bromine, phenyl and/or nitro, or represents phenoxyalkyl which has 1 or 2 carbon atoms in the alkyl part and is optionally mono-, di- or trisubstituted by identical or different substituents from the group comprising methyl, ethyl, propyl, fluorine, chlorine, bromine, phenyl and/or nitro, or $R^2$ and $R^3$ together represent the group

in which $R^4$ represents hydrogen, methyl, ethyl, propyl, cyclopentyl, cyclohexyl, cyclopentenyl or cyclohexenyl and $R^5$ represents methyl, ethyl, propyl, cyclopentyl, cyclohexyl, cyclopentenyl or cyclohexenyl, or represents phenyl which is optionally mono-, di- or trisubstituted by identical or different substituents from the group comprising methyl, ethyl, propyl, fluorine and/or chlorine, or furthermore, $R^4$ and $R^5$, together with the carbon atom to which they are bonded, also represent cyclopentyl, cyclohexyl, cyclopentenyl or cyclohexenyl, and X represents nitrogen or a CH group.

The racemates of azole derivatives of the formula (Ia) are already known (compare DE-OS (German Published Specification) No. 2,737,489, EP-OS (European Published Specification) No. 0,015,387, EP-OS (European Published Specification) No. 0,032,200, EP-OS (European Published Specification) No. 0,044,425 and EP-OS (European Published Specification) No. 0,053,311).

Formula (II) provides a definition of the permethric acid halides furthermore required as starting substances in carrying out the process according to the invention. Permethric acid chlorides are particularly preferred. Examples which may be mentioned are 1R-trans-permethric acid chloride, 1S-trans-permethric acid chloride, 1R-cis-pemethric acid chloride and 1S-cis-permethric acid chloride.

The optically active permethric acid halides of the formula (II) are already known (compare EP-OS (European Published Specification) No. 0,022,972).

The first stage of the process according to the invention is preferably carried out in the presence of bases.

All the customary organic or inorganic bases can be employed here. Bases which can preferably be used are alkali metal carbonates, such as, for example, sodium carbonate or sodium bicarbonate, and furthermore lower tertiary alkylamines, cycloalkylamines, arylalkylamines or arylamines, such as, for example, triethylamine, N,N-dimethylbenzylamine, pyridine, 1,4-diazabicyclo-[2,2,2]-octane or 1,5-diazabicyclo-[4,3,0]-non-5-ene.

Possible diluents for carrying out the first stage (esterification) of the process according to the invention are all the inert organic solvents. Solvents which can preferably be used are hydrocarbons, such as benzine, benzene, toluene or xylene, halogenated hydrocarbons, such as methylene chloride, chloroform, carbon tetrachloride, chlorobenzene or dichlorobenzene, ethers, such as diethyl ether, tetrahydrofuran or dioxane, nitriles, such as acetonitrile or propionitrile, or esters, such as ethyl acetate.

The reaction temperatures can be varied within a substantial range in carrying out the 1st stage of the process according to the invention. The reaction is in general carried out between $-10°$ C. and $+150°$ C., preferably between 0° and 100° C.

The first stage of the process according to the invention is in general carried out under normal pressure. However, it is also possible to carry out this stage under increased or reduced pressure.

In carrying out the 1st stage of the process according to the invention, in general 1 to 2 moles, preferably 1 to 1.5 moles, of optically active permethric acid halide of the formula (II) and, if appropriate, 1.5 to 2.5, preferably 1.5 to 2, moles of acid-binding agent are employed per mole of racemic azole derivative of the formula (Ia): The diastereomer mixture is isolated by customary methods. In general, a procedure is followed in which, when the reaction has ended, water is added and the organic phase is separated off and, after drying, concentrated under reduced pressure.

Separation of the diastereomeric esters of the formula (III) in the 2nd stage of the process according to the invention can be carried out by methods suitable for such purposes, thus, for example, by fractional crystallization or with the aid of chromatographic processes. A procedure is preferably followed in which the desired product is concentrated by fractional crystallization and then purified by a chromatographic route, such as, for example, by high pressure liquid chromatography over suitable columns.

In general, of the two diastereomers of the formula (III), one of the two products can be isolated particularly well by fractional crystallization. If this is the diastereomer from which the desired optically active azole derivative of the formula (I) can be liberated in the 3rd stage of the process according to the invention, controlled preparation of the substance in question is achieved. However, if it is that diastereomer which does not lead to the desired product, controlled preparation of the substance in question is initially possible only with limitation. In this case, a procedure is advantageously followed in which the complementary optically active permethric acid halide of the formula (II) is used in the first stage. This means that the diastereomer of the formula III from which the desired substance can be liberated in the 3rd stage of the process preferentially crystallizes under identical reaction conditions.

Possible diluents for the 2nd stage (ester hydrolysis) of the process according to the invention are likewise inert organic solvents. Alcohol, such as, for example, methanol, ethanol or propanol, is preferably used.

The active compounds according to the invention are liberated in the second stage of the process according to the invention with the aid of bases. Bases which are preferably used here are aqueous inorganic bases, such as sodiumhydroxide or potassium hydroxide in water.

The reaction temperatures can likewise be varied within a substantial range in carrying out the 2nd stage of the process according to the invention. The reaction is in general carried out between 0° C. and 120° C., preferably between 10° C. and 100° C.

In carrying out the 3rd stage of the process according to the invention, in general 1 to 3 moles, preferably 1 to 2 moles, of base are employed per mole of the particular diastereomer ester of the formula (III).

The active compounds according to the invention are isolated by customary methods. In general, a procedure is followed in which water is added to the reaction mixture and the mixture is then extracted several times with an organic solvent of low water-miscibility, the combined organic phases are dried and concentrated by stripping off the solvent under reduced pressure and, if necessary, the residue which remains is freed from any impurities present by recrystallization or by washing with an organic solvent.

In carrying out the third stage of the process according to the invention, in each case that disatereomeric ester of the formula (III) from which the desired optically active substance of the formula (I) according to the invention is liberated by treatment with a base is employed.

The optically active azole derivatives which can be prepared by the process according to the invention are distinguished by very good fungicidal or plant growth-regulating properties.

The process according to the invention is illustrated by the following examples.

EXAMPLE 1

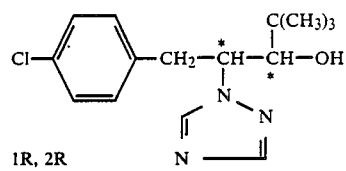

1R, 2R     (I-1)

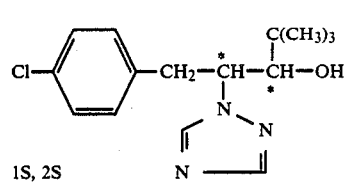

1S, 2S     (I-2)

(a) Esterification

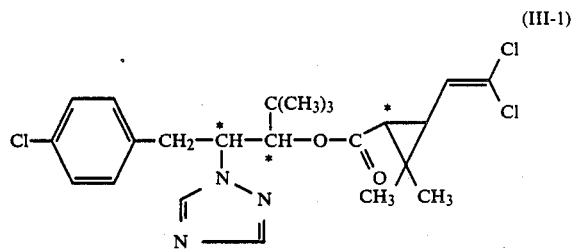

(III-1)

A mixture of 1 g (4.4 mmol) of 1S-trans-permethric acid chloride, 1.25 g (4.2 mmol) of racemic 1-(4-chlorophenyl)-2-(1,2,4-triazol-1-yl)-3-hydroxy-4,4-dimethyl-pentane and 10 ml of pyridine is stirred at 110° to 130° C. for 2 hours. Toluene and water are then added. The organic phase is separated off, dried and evaporated under reduced pressure. 2.1 g of a honey-yellow, crystalline product which, according to analysis by gas chromatography, consists to the extent of 80% of a diastereomer mixture of esters of the formula (III-1) are obtained in this manner. The yield is accordingly calculated as 84% of theory.

$H^1$-NMR spectrum (90 MHz): $\delta=0.74$ and 0.80 (9H, 2s); $\delta=1.24$; 1.30 and 1.39 (6H, 4s); $\delta=1.75$ and 1.77 (1H, 2d); $\delta=2.36$ (1H, 2dd); $\delta=3.0$ (2H, 2d); $\delta=4.72-4.95$ (1H, m); $\delta=5.09$ (1H, 2d); $\delta=5.71$ and 5.74 (1H, 2d); $\delta=6.8$ to 7.2 (4H, d); $\delta=7.8$ (1H, s); and $\delta=8.13$ and 8.19 (1H, 2s)

(b) Resolution

A diastereomer mixture of trans-1S-permethric acid 1-(4-chlorophenyl)-2-(1,2,4-triazol-1-yl)-4,4-dimethyl-pent-3-yl esters (compare a) is resolved by chromatographing a 20% strength solution of the diastereomer mixture in chloroform.

Apparatuses: Lobar system consisting of pump: CFG type 1pr, detector: Knauer RJ detector, auto-fraction collector: LKB 2111 Multirac Eluting agent: n-hexane: tert.-butyl methyl ether = 6:4
Flow rate: 6 ml per minute
Column: Lichroprep. Si 60, size C
Amount applied: 4 g
Retention time: $t_R=4-5.5$ hours The fractions of identical content collected are combined and evaporated. Each of the two diastereomers are obtained in a yield of 70% of theory in this manner. The chemical purity is in each case more than 98%; the optical purity is 98%.

Gas chromatography:

50 m SE 30 glass capillary, 2 ml of helium/minute, 120° C./12° C. minute$^{-1}$/300° C.; 21′.isothermal 1S,2S-1S-trans ester (fraction 1): t′$_R$=22.4′, 98%; t″$_R$=22.7′, 2%

1R,2R-1S-trans ester (fraction 2): t′$_R$=22.4′, 2%; t″$_R$=22.7′, 98%

(c) Hydrolysis

In each case 1 g of the esters mentioned above (compare b) and 30 ml of 5% strength by weight methanolic potassium hydroxide solution are heated under reflux for 5 hours. Thereafter, the reaction mixture is evaporated under reduced pressure at 40° C. Water and diethyl ether are added to the residue which remains. The organic phase is separated off, washed with water, dried and concentrated under reduced pressure. 0.6 g (91% of theory) of the particular compound are obtained in this manner in the form of a crystalline product. The chemical purity is ~98% the optical purity is ~96% ee (after evaluation by gas chromatography, based on 100%—surface of the diastereomeric permethric acid ester).

1S,2S compound: $[\alpha]_D^{23}$= +80° C. (C=0.015 mole/l; CHCl$_3$)

1R,2R compound: $[\alpha]_D^{23}$= −80° C. (C=0.015 mole/l; CHCl$_3$)

EXAMPLE 2

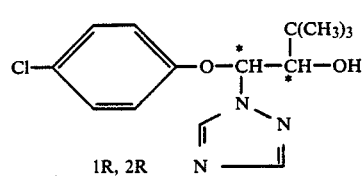
(I-3)
1R, 2R

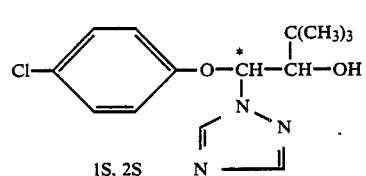
(I-4)
1S, 2S

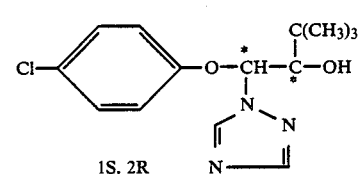
(I-5)
1S, 2R

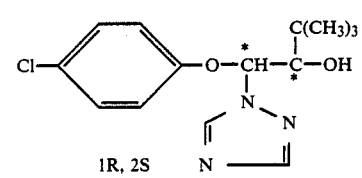
(I-6)
1R, 2S (a) Esterification

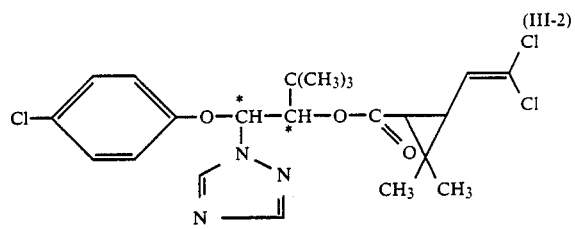
(III-2)

A mixture of 1 g (4.4 mmol) of 1S-trans-permethric acid chloride, 1.25 g (4.2 mmol) of 1-(4-chlorophenoxy)-1-(1,2,4-triazol-1-yl)-2-hydroxy-3,3-dimethyl-butane (mixture of 50% of threo 1R, 2S and 1S, 2R and 50% of erythro 1R, 2R and 1S, 2S) is stirred at 100° C. to 110° C. for 3 hours. Thereafter, 5 ml of triethylamine are initially added, and toluene and water are then added. The organic phase is separated off, washed with water, dried and evaporated under reduced pressure. 2.1 g of a crystalline product which, according to analysis by gas chromatography, consists to the extent of 90% of a diastereomer mixture of esters of the formula (III-2) are obtained in this manner. The yield is accordingly calculated as 93% of theory.

(b) Resolution

A diastereomer mixture of trans-1S-permethric acid 1-(4-chlorophenoxy)-1-(1,2,4-triazol-1-yl)-3,3-dimethyl-but-2-yl esters (compare a) is resolved by chromatographing 1.1 ml of a 10% strength solution of the diastereomer mixture in cyclohexane/methylene chloride=85:15.

Apparatuses: Perkin-Elmer Autosampler, Mo. 420, Perkin-Elmer LC chromatograph, series 3B, Perkin-Elmer UV detector LC 75, Auto-fraction collector Gilson CPR Ref 45.500

Eluting agent: cyclohexane/methylene chloride 85:15

Flow rate: 15 ml minute$^{-1}$ (2 pumps)

Column: Lichrosorb Diol 5μφ2.5 cm

Retention times: t$_R$+threo ester 14 minutes; t$_R$−threo ester 13 minutes; t$_R$+erythro ester 18 minutes and t$_R$−erythro ester 16 minutes.

All the fractions are collected via the peak height control of the Gilson collector between 60 and 80% "height". The solvent is in each case stripped off under reduced pressure. In each case a white, crystalline residue remains. The structure of the substances isolated is confirmed by NMR spectroscopy data. The optical purity of each fraction, which was checked by capillary gas chromatography, is in each case greater than 98%.

Gas chromatography: 50 m S 30 glass capillary, 2 ml of helium/minute, 200° C./8° C. minute$^{-1}$/300° C.

t′$_R$=9.40 minutes; t″$_R$=9.55 minutes; t‴$_R$=9.64 minutes and t″″$_R$=9.70 minutes.

Isomer A (threo):

H$^1$-NMR spectrum (90 MHz): δ=1.05 (9H, s); δ=1.14 (3H, s); δ=1.21 (3H, s); δ=1.70 (1H, d); δ=2.17 (1H, d); δ=5.17 (1H, d); δ=5.64 (1H, d); δ=6.38 (1H, d); δ=6.78 (2H aromatic); δ=7.17 (2H aromatic); δ=7.94 (1H, s); and δ=8.19 (1H, s).

Isomer B (threo):

H$^1$-NMR spectrum (90 MHz): δ=0.98 (9H, s); δ=1.21 (3H, s); δ=1.27 (3H, s); δ=1.66 (1H, d); δ=2.23 (1H, dd); δ=5.21 (1H, d); δ=5.61 (1H, d); δ=6.30 (1H, dd); δ=6.70–7.25 (4H aromatic); δ=7.95 (1H, s); and δ=8.21 (1H, s).

Isomer C (erythro):

H$^1$-NMR spectrum (90 MHz): δ=0.95 (9H, s); δ=1.19 (3H, s); δ=1.24 (3H, s); δ=1.53 (1H, d); δ=2.17 (1H, dd); δ=5.39 (1H, d); δ=5.62 (1H, d); δ=6.26 (1H, d); δ=6.7-7.2 (4H aromatic); δ=7.90 (1H, s); and δ=8.34 (1H, s).

Isomer D (erythro):

H$^1$-NMR spectrum (90 MHz): δ=0.98 (9H, s); δ=1.17 (6H, s); δ=1.54 (1H, d); δ=2.19 (1H, dd); δ=5.40 (1H, d); δ=5.62 (1H, d); δ=6.26 (1H, d); δ=6.70-7.28 (4H aromatic); δ=7.93 (1H, s); and δ=8.32 (1H, s).

(c) Hydrolysis

A mixture of the particular trans-1S-permethric acid 1-(4-chlorophenoxy)-1-(1,2,4-triazol-1-yl)-3,3-dimethyl-but-2-yl ester (compare b) and 100 ml of 5% strength by weight methanolic potassium hydroxide solution is heated under reflux for 1.5 hours. Thereafter, the reaction mixture is evaporated off under reduced pressure at 40° C. Water and diethyl ether are added to the residue which remains. The organic phase is separated off, washed with water, dried and concentrated under reduced pressure. The particular desired product is contained in this manner in the form of a crystalline substance.

EXAMPLE 3

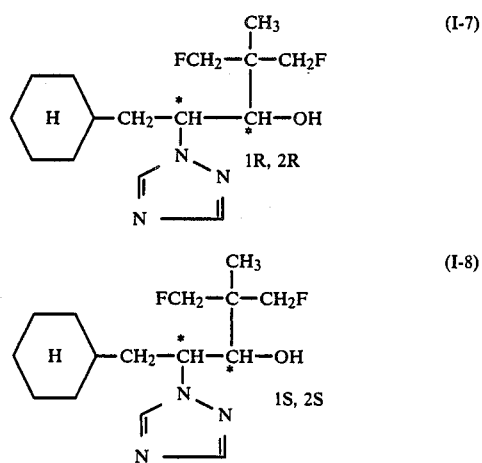

(a) Esterification

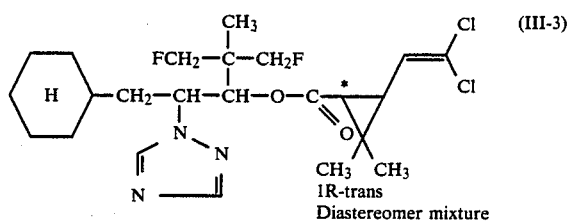

A mixture of 760 mg (3.3 mmol) of 1R-trans-permethric acid chloride and 1 g (3.3 mmol) of racemic 1-cyclohexyl-2-(1,2,4-triazol-1-yl)-3-hydroxy-4,4-bis-fluoromethyl-pentane is stirred at 100° C. for 12 hours. Thereafter, 5 ml of triethylamine is added. Diethyl ether and water are added to the resulting reaction mixture. The organic phase is separated off, dried and evaporated under reduced pressure. 1.5 g of a honey-yellow product which, according to the gas chromatogram, consists to the extent of 92% of a diastereomer mixture of compounds of the abovementioned formula (III-3) are obtained in this manner. The yield is accordingly calculated as 87% of theory.

H$^1$-nuclear magnetic resonance spectrum (90 MHz): δ=0.57 (3H, sbr.); δ=0.8-1.8 (20H, mbr.); δ=2.2-2.3 (1H, 2dd); δ=3.8-4.8 (5H, mbr.); δ=5.2 (1H, d); δ=5.7 and 5.8 (1H, 2d); δ=7.9 (1H, s); and δ=8.14 and 8.20 (1H, 2s).

(b) Resolution

A diastereomer mixture of 1R-trans-permethric acid 1-cyclohexyl-2-(1,2,4-triazol-1-yl)-4,4-bis-fluoromethyl-pent-3-yl esters (compare a) is resolved by chromatographing a 30% strength solution of the diastereomer mixture in n-hexane/diethyl ether=6:4.

Apparatuses: Lobar system consisting of: pump: CFG type: 1pr, detector: Knauer RI detector, Auto-fraction collector: LKB 2111 Multirac Eluting agent: n-hexane: diethyl ether=6:4

Flow rate: 6 ml minute$^{-1}$

Column: Lichroprep. Si 60 size C

Amount applied: 1.5-2.0 g

Retention time: $t_R$=3-3.5 hours

The eluted product with a content of 99% of the desired diastereomer is obtained from the fractions by the peak fronting method. The fractions containing 60 to 99% of "target diastereomer" are subjected to another resolution. 40% of the diastereomer ester employed are obtained with a chemical purity of >98% and an optical purity of >99% by this procedure. The optical purity is determined here by capillary gas chromatography.

Gas chromatography: 50 ml SE 30 glass capillary, 2 ml of helium/minute, 120° C./12° C. minute$^{-1}$/300° C./21' isothermal $t'_R$=21.5'>99%; $t''_R$=21.9'<1%

(c) Hydrolysis

A mixture of 1 g of the particular 1R-trans-permethric acid [1-cyclohexyl-2-(1,2,4-triazol-1-yl)-4,4-bis-fluoromethyl-pent-3-yl] ester (compare b) in 10 ml of 5% strength by weight methanolic potassium hydroxide solution is stirred at 40° C. for 1 hour. Thereafter, the reaction mixture is concentrated under reduced pressure. Water and 20 ml of diethyl ether are added to the residue which remains. The organic phase is separated off, washed with water, dried and concentrated under reduced pressure. 0.57 g (91% of theory) of the desired compound is obtained in this manner in the form of a crystalline product. The chemical purity is >98%; the optical purity is >98% ee (according to evaluation by gas chromatography, based on 100% area of the diastereomer permethric acid ester).

$[\alpha]_D^{23}$= -22.2° (c=0.038 mole/l; CHCl$_3$)

$[\alpha]_D^{23}$= +22.6° (c=0.039 mole/l; CHCl$_3$)*

*The (+)-isomer was prepared by using 1S-trans-permethric acid chloride in an identical procedure.

The optically active azole derivatives listed by way of their formulae in the following examples were also prepared by the abovementioned methods.

EXAMPLE 4

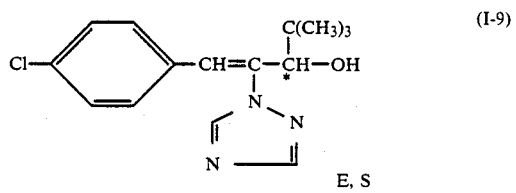

-continued

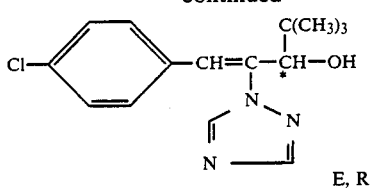
(I-10)

E, R

EXAMPLE 5

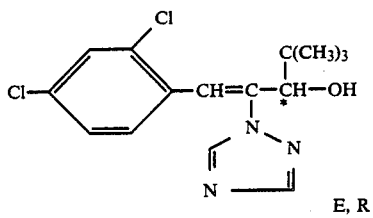
(I-11)

E, R

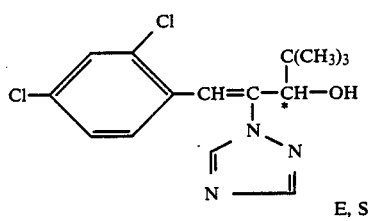
(I-12)

E, S

It will be understood that the specification and examples are illustrative but not limitative of the present invention and that other embodiments within the spirit and scope of the invention will suggest themselves to those skilled in the art.

I claim:

1. A process for the preparation of a substantially pure optically active azole derivative of the formula

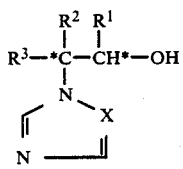

in which $R^1$ represents straight-chain or branched alkyl with 1 to 4 carbon atoms, or represents cycloalkyl which has 3 to 7 ring carbon atoms and is optionally monosubstituted or polysubstituted by alkyl with 1 or 2 carbon atoms, or represents phenyl or naphthyl, it being possible for the above two radicals mentioned to be monosubstituted or polysubstituted by identical or different substituents from the group consisting of halogen, straight-chain or branched alkyl with 1 to 4 carbon atoms and halogenoalkyl with 1 or 2 carbon atoms and 1 to 5 identical or different halogen atoms, $X^1$ represents hydrogen or halogen, $X^2$ represents halogen, Y represents straight-chain or branched alkyl with 1 to 6 carbon atoms, alkoxy with 1 to 6 carbon atoms, alkylthio with 1 to 6 carbon atoms, halogenoalkoxy with 1 to 6 carbon atoms and 1 to 9 identical or different halogen atoms, halogenoalkylthio with 1 to 6 carbon atoms and 1 to 9 identical or different halogen atoms, alkenyl with 2 to 6 carbon atoms, straight-chain or branched alkoxycarbonyl with 1 to 4 carbon atoms in the alkoxy part or cyano, or represents phenyl, phenoxy, phenylthio, phenylalkoxy with 1 to 4 carbon atoms in the alkoxy group or phenylalkylthio with 1 to 4 carbon atoms in the alkylthio group, it being possible for each of the abovementioned phenyl radicals to be monosubstituted or polysubstituted by identical or different substituents from the group consisting of halogen, alkyl with 1 to 4 carbon atoms, alkoxy with 1 or 2 carbon atoms, alkylthio with 1 or 2 carbon atoms, halogenoalkyl with 1 or 2 carbon atoms and 1 to 5 identical or different halogen atoms, such as fluorine and chlorine atoms, halogenoalkoxy with 1 or 2 carbon atoms and 1 to 5 identical or different halogen atoms, halogenoalkylthio with 1 or 2 carbon atoms and 1 to 5 identical or different halogen atoms, cycloalkyl with 3 to 7 carbon atoms, dialkylamino with 1 to 4 carbon atoms in each alkyl part, cyano, nitro and straight-chain or branched alkoxycarbonyl with 1 to 4 carbon atoms in the alkoxy part, m represents the number 0 or 1, n represents the number 0, 1 or 2, $R^2$ represents hydrogen or methyl, and $R^3$ represents alkyl with 1 to 6 carbon atoms, alkoxy with 1 to 6 carbon atoms, cycloalkylalkyl with 3 to 8 carbon atoms in the cycloalkyl group and 1 to 4 carbon atoms in the alkyl part, aryl which has 6 to 10 carbon atoms and is optionally mono- or polysubstituted by identical or different substituents from the group consisting of alkyl with 1 to 4 carbon atoms, halogen, phenyl and/or nitro, or aralkyl which has 6 to 10 carbon atoms in the aryl part and 1 to 4 carbon atoms in the alkyl part and is optionally mono- or polysubstituted by identical or different substituents from the group consisting of alkyl with 1 to 4 carbon atoms, halogen, phenyl and/or nitro, or represents aroxy which has 6 to 10 carbon atoms and is optionally mono- or polysubstituted by identical or different substituents from the group consisting of alkyl with 1 to 4 carbon atoms, halogen, phenyl and/or nitro, or represents aroxyalkyl which has 6 to 10 carbon atoms in the aroxy part and 1 to 4 carbon atoms in the alkyl part and is optionally mono- or polysubstituted by identical or different substituents from the group consisting of alkyl with 1 to 4 carbon atoms, halogen, phenyl and/or nitro, or $R^2$ and $R^3$ also together represent the group

in which $R^4$ represents hydrogen, alkyl with 1 to 4 carbon atoms, cycloalkyl with 3 to 8 carbon atoms or cycloalkenyl with 5 to 8 carbon atoms and $R^5$ represents alkyl with 1 to 4 carbon atoms, cycloalkyl with 3 to 8 carbon atoms, cycloalkenyl with 5 to 8 carbon atoms, or aryl which has 6 to 10 carbon atoms and is optionally mono- or polysubstituted by identical or different substituents from the group consisting of alkyl with 1 to 4 carbon atoms and/or halogen, or R⁴ and R⁵, together with the carbon atom to which they are bonded, represent cycloalkyl with 5 to 8 carbon atoms, or represent cycloalkenyl with 5 to 8 carbon atoms, X represents nitrogen or a CH group, comprising in a first stage reacting a racemate of an azole derivative of the formula

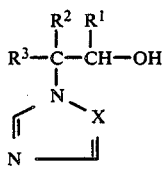

with an optically active permethric acid halide of the formula

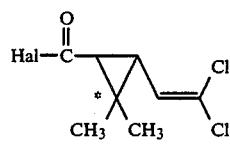

in which

Hal represents chlorine or bromine, thereby to produce a diastereomeric mixture of an ester of the formula

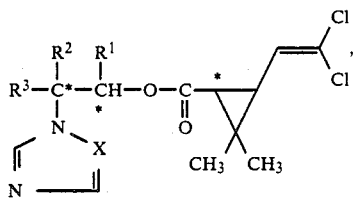

in a second stage separating the components of the ester mixture based on their different physical properties, and in a third stage reacting an individual component ester with a base in the presence of a diluent to liberate the desired substantially pure optically active azole derivative.

2. The process according to claim 1, wherein the optically active permethric acid halide is 1R-trans-permethric acid chloride.

3. The process according to claim 1, wherein the optically active permethric acid halide is 1S-trans-permethric acid chloride.

4. The process according to claim 1, wherein the first stage is carried out at a temperature between −10° C. and +150° C.

5. The procees according to claim 1, wherein the third stage is carried out at a temperature between 0° C. and 120° C.

6. The process according to claim 1, wherein in the first stage 1 and 2 moles of the optically active permethric acid halide and 1.5 to 2.5 moles of an acid-binding agent are employed per mole of racemic azole derivative.

* * * * *

UNITED STATES PATENT AND TRADEMARK OFFICE
CERTIFICATE OF CORRECTION

PATENT NO. : 4,774,338
DATED : Sep. 27, 1988
INVENTOR(S) : Priesnitz

It is certified that error appears in the above-identified patent and that said Letters Patent is hereby corrected as shown below:

| | |
|---|---|
| Col. 4, Line 52 | Delete "by identical" |
| Col. 8, Line 30 | Insert --(Diastereomer mixture)-- after formula |
| Col. 10, Line 11 | Insert --Diastereomer mixture-- after formula |
| Col. 11, Line 22 | Delete "contained" and substitute --obtained-- |
| Col. 13, Line 59 | Insert --or $R^1$ furthermore represents a radical of the formula |

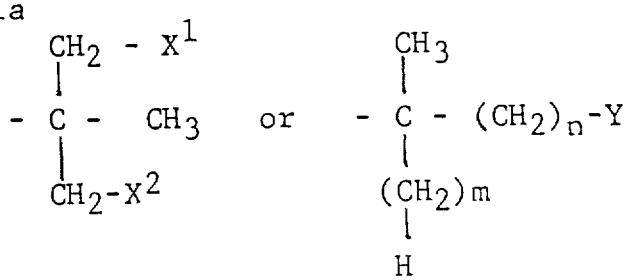

wherein --

Signed and Sealed this

Eighth Day of August, 1989

Attest:

DONALD J. QUIGG

Attesting Officer    Commissioner of Patents and Trademarks